United States Patent
Lange et al.

(10) Patent No.: US 6,348,521 B1
(45) Date of Patent: *Feb. 19, 2002

(54) STABLE AND HIGH SOLIDS AQUEOUS DISPERSIONS OF BLOCKED POLYISOCYANATES

(75) Inventors: Hartwig Lange, Haltern; Klaus Janischewski; Dirk Reichel, both of Dorsten, all of (DE)

(73) Assignee: Degussa-Huels Aktiengesellschaft, Frankfurt am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/567,979

(22) Filed: May 10, 2000

Related U.S. Application Data

(63) Continuation of application No. 08/958,398, filed on Oct. 29, 1997, now Pat. No. 6,096,805.

(30) Foreign Application Priority Data

Oct. 29, 1996 (DE) .......................................... 196 44 838

(51) Int. Cl.[7] .............................................. C08G 18/80
(52) U.S. Cl. .................. 523/336; 523/339; 252/182.22; 525/417; 528/45; 524/591
(58) Field of Search ........................ 524/591; 528/45; 525/417; 252/182.22; 523/339, 336

(56) References Cited

U.S. PATENT DOCUMENTS

| | | | |
|---|---|---|---|
| 4,098,933 A | * 7/1978 | Burkhardt | 427/379 |
| 5,705,557 A | 1/1998 | Lange et al. | 524/507 |
| 6,096,805 A | * 8/2000 | Lange | 524/591 |

* cited by examiner

*Primary Examiner*—Rachel Gorr
(74) *Attorney, Agent, or Firm*—Oblon, Spivak, McClelland, Maier & Neustadt, P.C.

(57) ABSTRACT

A stable and high-solids aqueous dispersion of blocked isocyanates, containing auxiliary solvent, is prepared by (1) preparing a solution of a polyisocyanate mixture of from 20–70% by weight of a blocked, hydrophilically modified polyisocyanate (A) and from 30–80% by weight of a blocked, hydrophobic polyisocyanate (B) in an auxiliary solvent (G) and (2) adding water to this solution, with intensive mixing, in an amount which is such as to give a two-phase system comprising a disperse polyisocyanate phase and a continuous, aqueous phase containing auxiliary solvent. In a preferred embodiment of the invention dispersions are prepared which are virtually free from auxiliary solvent, by first adding a portion of water to the solution (1), substantially removing the auxiliary solvent with intensive mixing and then adding a second portion of water with intensive mixing to the mixture comprising the polyisocyanates (A) and (B) and the first portion of water.

3 Claims, No Drawings

STABLE AND HIGH SOLIDS AQUEOUS DISPERSIONS OF BLOCKED POLYISOCYANATES

This application is a continuation of application Ser. No. 08/958,398, filed Oct. 29, 1997 and issued as U.S. Pat. No. 6,096,805.

BACKGROUND OF THE INVENTION

1. Field of the Invention

The present invention relates to stable and high-solids aqueous dispersions of blocked polyisocyanates, either containing auxiliary solvent or being virtually free from auxiliary solvent, to a process for preparing such dispersions and the use of such dispersions as cross-linkers for film-forming resins.

2. Description of the Background

Blocked (or capped) polyisocyanates are known and widely used as cross-linking agents for film-forming resins in solvent-borne coating systems. For reasons of environmental protection and, of course, of cost as well, numerous technical developments of the recent past have been directed to reducing the amount of solvent or, as is particularly desirable, at providing solvent-free or virtually solvent-free systems.

Aqueous dispersions of blocked polyisocyanates are suitable for use in single-component waterborne (or water-thinnable) coating materials, i.e. in aqueous, solvent-free or virtually solvent-free coating systems, which, in addition to the blocked polyisocyanates, which function as cross-linking agents, comprise a water-dissolved or-dispersed film-forming resin having functional groups that are able to react with isocyanate groups. Since blocked isocyanates are, in the majority of cases, solids or highly viscous substances, they can be dispersed in water only with the addition of solvents or, without solvent, only above their melting point. The disadvantages of the two processes are that, in the first case, the solvent used for dilution must be removed again after dispersion, at considerable expense, while in the case of melt emulsification, some of the blocking agent is cleaved off early at the high temperatures required, and the isocyanate groups that have been released react with water in the course of dispersion and are no longer available for cross-linking with the functional groups of the film-forming resin.

The aqueous dispersions of the blocked polyisocyanates (and, of course, those of the film-forming resins as well) should, where possible, be of high solids content. The principal advantage of high-solids content dispersions is that, with only one application, it is possible to produce thick coats having excellent properties (fullness, resistance, hiding power). Relative to multicoat applications, this means not only a saving in time and (because of the multiple stoving procedures) in energy, but also in optimizing quality, since each additional coat increases the risk of production errors. In addition, high-solids dispersions also lessen the costs of transportation and storage. The dispersions should, moreover, be stable, i.e. storable for long periods without sedimenting or coagulating to any marked extent. Should coagulation or sedimentation nevertheless occur, the deposits should be readily and durably redispersible.

Known processes for preparing stable aqueous dispersions of blocked polyisocyanates make use of external emulsifiers and protective colloids (JP 4 216 815, JP 4 216 816, JP 4 216 817 and WO 94/22935). A disadvantage of these processes is the permanent hydrophilicity of the emulsifiers and of the protective colloids, which is retained in the coatings which result on stoving by reaction of the polyisocyanates with the isocyanate-reactive groups of the film-forming resins. Consequently, these coatings have a tendency, under the effect of water, to become cloudy, to soften and/or to swell up, ruling out the use of such dispersions at least for coating materials that are to be employed outdoors.

The process that DE 24 56 469 describes for preparing aqueous dispersions starts with partially blocked polyisocyanates, which are reacted with a hydrophilicizing agent, which contains an NCO-reactive group and also a hydrophilic or potentially hydrophilic group, for example, a sulfo acid or carboxyl group. Both types of groups can be converted by neutralization into hydrophilic ionic groups, for example sulfonate or carboxylate groups. The hydrophilicizing agents used in the examples are the sodium salts of N-methylaminoethanesulfonic acid. The reaction product is then dispersed in water. A similar process is described in EP 0 012 348, where the blocked hydrophilicized polyisocyanates are not only self-dispersible, but also promote the dispersion of hydrophobic film-forming resins. In the case of these processes, however, which is not used industrially, the linking of the compound having a (potentially) hydrophilic group takes place, because of the partial blocking beforehand, at low NCO contents, which firstly requires an uneconomically long reaction time and secondly has the consequence either that not all of the free NCO groups are hydrophilically linked or, in the case of excess hydrophilicizing agent, that unreacted hydrophilicizing agent remains in the polyisocyanate dispersion.

DE 27 08 611 describes a process for preparing polyurethane prepolymers, in which polyisocyanates are first of all reacted with an excess of hydroxycarboxylic acids such as dimethylolpropionic acid, and then the free isocyanate groups that remain are blocked. These polyurethane prepolymers must have high acid numbers of >30 mg of KOH/g, since at lower acid numbers, stable dispersions or solutions can be prepared only with additional organic solvents. A disadvantage of this process is that a very considerable proportion of the original isocyanate groups is lost for cross-linking with the film-forming resin as a result of the reaction with the hydroxycarboxylic acid hydrophilicizing reagent. A further disadvantage of this process is the high viscosity of dispersions with a solids content >35% by weight, which makes processing more difficult if not virtually impossible.

EP 0 312 836 describes a process in which isocyanate groups are capped by reaction with a cyanourea salt. The hydrophilic groups thereby created participate in the cross-linking reaction in the course of stoving, and thus do not impair the density of cross-linking. A disadvantage, however, is that amines are given off during stoving, which only with difficulty leave the paint film, and, in the case of Light-colored coatings, cause disruptive yellowing of the coatings.

EP 0 133 223 describes blocked polyisocyanates which are hydrophilicized by means of cyclic malonates. curing in these systems takes place likewise through the cyclic malonate groups, with the result that the hydrophilic modification again does not cause any reduction in the cross-linking density. Detrimental to this process, however, are the considerable amounts of water-soluble organic solvent required.

EP 0 524 511 discloses a process in which nonionically modified polyisocyanates having free isocyanate groups are first of all dispersed in water and then the isocyanate groups are blocked. In the course of this reaction, however, some of the isocyanate groups react with water and are lost for the crosslinking reaction. Moreover, it is difficult to establish reproducibly the particular stoichiometric proportions that are desired.

Furthermore, EP 0 537 578 discloses a process in which blocked polyisocyanates, for textile finishing (crease-resistant finishing), are hydrophilicized with, inter alia, polyalkylene oxide units incorporated therein and are dispersed. EP 0 424 697 and DE 28 14 815 also describe dispersions of blocked, nonionically hydrophilicized polyisocyanates. These dispersions, however, are in turn permanently hydrophilic, so that coatings produced with them may turn cloudy, soften and/or swell under the action of moisture and are, therefore, unsuitable for exterior applications.

EP 0 022 452 describes a one-component polyurethane system whose hardener is a polyurethane prepolymer in which each molecule is linked with a hydrophilic modifying reagent. In addition to the loss of cross-linkable isocyanate groups, a disadvantage here is that a solvent mixture of water and alcohol is required and, in particular, that dispersions with a solids content of >40% by weight have such a high viscosity that they are difficult to process.

Finally, EP 0 566 953 and EP 0 576 952 describe specific polyisocyanate mixtures, hydrophilicized by means of hydroxycarboxylic acids, which are suitable for the curing of film-forming resins in aqueous systems. A need, therefore, continues to exist for an aqueous dispersed polyurethane system of improved stability and high solids content.

SUMMARY OF THE INVENTION

Accordingly, one object of the present invention is to provide an aqueous dispersion of a blocked polyisocyanate which is stable and has a high solids content.

Briefly, this object and other objects of the present invention as hereinafter will become more readily apparent can be attained by a process for preparing stable and high-solids aqueous dispersions of blocked polyisocyanates, containing auxiliary solvent, comprising:

(1) preparing a solution of a polyisocyanate mixture of from 20–70% by weight of a blocked, hydrophilically modified polyisocyanate (A) and from 30–80% by weight of a blocked, hydrophobic polyisocyanate (B) in an auxiliary solvent (G), and (2) adding to this solution, with intensive mixing, an amount of water which is sufficient to give a two-phase system comprising a dispersed polyisocyanate phase and a continuous, aqueous phase containing auxiliary solvent.

DETAILED DESCRIPTION OF THE PREFERRED EMBODIMENTS

In an advantageous embodiment of this process, corresponding dispersions which are, however, virtually free from auxiliary solvent (G) are prepared by (3) adding a first portion of the total amount of water used to the solution of stage (1), (4) substantially removing the auxiliary solvent (G) from the aqueous mixture that is formed, containing auxiliary solvent, with intensive mixing, and (5) adding a second portion of water to the remaining mixture comprising the blocked polyisocyanates (A) and (B) and the first portion of water, with the provisos that (i) the first portion of water is of a size such that the polyisocyanates (A) and (B) form the continuous phase in the mixture which remains after the substantial removal of the auxiliary solvent (G), and (ii) the addition of the second portion of water takes place with intensive mixing, at least up until the point of phase inversion.

Another aspect of the invention are stable and high-solids aqueous dispersions of blocked polyisocyanates, both containing auxiliary solvent and, in particular, dispersions which are virtually free of auxiliary solvent, which dispersions comprise, as a disperse phase, a polyisocyanate mixture of from 20–70% by weight of a blocked, hydrophilically modified polyisocyanate (A) and from 30–80% by weight of a blocked, hydrophobic polyisocyanate (B), which dispersions are prepared by the process of the invention. The stable and high-solids dispersions of the blocked polyisocyanates (A) and (B) function as cross-linkers for film-forming resins.

Properties and Advantages of the Dispersions of the Invention

The process of the invention provides, surprisingly, dispersions which have an optimum combination of the following advantageous properties:

(i) The solids content is high. In the case of the systems containing auxiliary solvent, the solids content is generally at least 35 and up to 80% by weight, preferably from 35–60% by weight. In the case of the systems which are virtually free from auxiliary solvent, the solids content is generally in the range from at least 35% by weight up to 60% by weight, advantageously from 40–50% by weight.

(ii) The viscosities of the high-solids dispersions at 25° C., despite the high solids content, are generally <1000 mPa·s, with the result that they can be processed without problems.

(iii) The latent isocyanate content, i.e. the amount by weight of isocyanate groups, calculated in unblocked form, in the blocked polyisocyanate mixture comprising (A) and (B), is sufficiently high despite the hydrophilicization. It is in general >8% by weight and can be up to 15% by weight. The mean latent NCO functionality, depending on the poiyisocyanate employed, is generally in the range from 2.5–4.5 and can be up to 6.0 or more, so that the particular requirement of high cross-linking density in the stoved coatings is ensured. The high latent isocyanate content and the high cross-linking density provide outstanding mechanical properties such as hardness and chemical resistance of product cross-linked coatings. To this extent, the coatings prepared with the dispersions of the invention are at least equal to the coatings prepared from the prior art.

(iv) When low-boiling auxiliary solvents (G) are used, they can be substantially removed by distillation. In the case of the preferred embodiment of the invention, the solvent is removed following the addition of a first portion of the total amount of water used, as a result of which the content of residual auxiliary solvent (G) in the finished dispersion, as formed by adding the second portion of water, can be reduced without difficulty to <2% by weight, in particular <0.5% by weight. The dispersions are, therefore, virtually free from auxiliary solvent. Contents of residual auxiliary solvent (G) of <0.5% by weight are advantageous since the dispersions do not give rise to any unpleasant odor in the course of the processing.

(v) The dispersions of the invention are storable for long periods both at room temperature and at slightly elevated temperature up to 60° C. For example, dispersions virtually free from auxiliary solvent with solids contents of from 45–50% by weight produce <1% by weight of solid sediment under optimum conditions at room temperature within 6 months or at 60° C. within 4–8 weeks. The slight sedimentation is in general, moreover, readily and durably redispersible. This good to excellent long-term stability is achieved with a minimum of hydrophilicity, namely by hydrophilicizing only part of the polyisocyanate, without the addition of an external dispersant and/or protective colloid and without the incorporation of hydrophilicizing polyoxyalkylene units and also, at least in the case of the preferred dispersions, without the addition of solvent.

(vi) The minimal hydrophilicity has the desired consequence. moreover, that the cured coatings are not very sensitive to moisture and are, therefore, also well-suited to exterior applications.

An essential feature of the invention is that the blocked polylsocyanate is a mixture of from 20–70% by weight of a blocked, hydrophilically modified polyisocyanate (A) and from 30–80% by weight of a blocked, hydrophobic polyisocyanate (B). The hydrophilically modified polyisocyanates (A) apparently facilitate the dispersion of the hydrophobic polyisocyanates (B) to give dispersions having optimum properties in terms of performance, such as viscosity, particle size and hardness of the subsequent coating films, and provide long-term stabilization of the dispersions. Advantageously, the proportion of the blocked, hydrophilically modified polyisocyanate (A) is from 35–60% by weight and, in particular, from 40–50% by weight. The proportion of the blocked, hydrophobic polyisocyanate (B), accordingly, is advantageously from 40–65% by weight and, in particular, from 50–60% by weight.

The Hydrophilically Modified Polyisocyanates (A) and the Hydrophobic Polvisocyanates (B)

Both the blocked, hydrophilically modified polyisocyanates (A) and the blocked, hydrophobic polyisocyanates (B) are derived from the customary hydrophobic polyisocyanates (C) employed in paint chemistry. Instead of using only one blocked, hydrophilically modified polyisocyanate (A) and/or only one blocked, hydrophobic polyisocyanate (B), it is not infrequently possible to employ, with advantage, polyisocyanates (A) and/or (B) which are based on mixtures of different hydrophobic polyisocyanates (c). The hydrophobic polyisocyanates (C) become hydrophilically modified polyisocyanates (D) by being reacted with a hydrophilicizing agent (E) and, if desired, with a neutralizing agent (H), as explained later on. By reaction with a blocking agent (F) the hydrophilically modified polyisocyanate (D) becomes the blocked, hydrophilically modified polyisocyanate (A) and the hydrophobic polyisocyanate (C) becomes the blocked, hydrophobic polyisocyanate (B).

In principle, suitable polyisocyanates for the invention include all aliphatic, cycloaliphatic, araliphatic, aromatic or heterocyclic polyisocyanates, as are described, for example, by W. Siefken in Liebigs Annalen der Chemie, 562, pages 75 . 136. A detailed exposition of the polyisocyanates that can be employed is given in EP 0 537 578, page 3, lines 10–45. Preferred polyisocyanates, because of the high light stability and weathering resistance of the paint films produced therefrom, include aliphatic and/or cycloaliphatic polyisocyanates having a mean molecular weight of up to about 1000 g/mol, advantageously of about 800 g/mol, and with a mean isocyanate functionality of from 2–4. Examples of these include simple diisocyanates such as 1,6-diisocyanatohexane (HDI), bis(4-isocyanatocyclohexyl) methane (HMDI), 1,5diisocyanato-2-methylpentane (MPDI), 1,6-diisocyanato-2,4,4-trimethylhexane and/or 1,6-diisocyanato-2,2,4-trimethylhexane (TMDI), and also, in particular, 3-isocyanatomethyl-3,5,5-trimethylcyclohexyl isocyanate (isophorone diisocyanate, IPDI). They also include dimers of uretdione structure prepared by catalytic reaction of these simple diisocyanates, principally of IPDI, HDI and/or HMDI. Another preferred class of polyisocyanates are the compounds having more than two isocyanate groups per molecule, that are prepared by allophanatization, trimerization, biuretization or urethanization of the simple diisocyanates, for example the reaction products of these simple diisocyanates such as IPDI, HDI and/or HMDI, with polyhydric alcohols (for example glycerol, trimethylolpropane, pentaerythritol) or with polyfunctional polyamines, or the triisocyanurates prepared by trimerizing the simple diisocyanates such as IPDI, HDI and HMDI. Examples of the (less preferred) aromatic polyisocyanates that may be mentioned include 2,4- and/or 2,6-diisocyanatotoluene and also 4,4'- and/or 2,4'-diisocyanatodiphenylmethane.

The Hydrophilicizing Agent (E)

As mentioned, the hydrophobic polyisocyanates (C) can be converted by reaction with a hydrophilicizing agent (E) and, if desired, with a neutralizing agent (H), as set out below, into hydrophilically modified polyisocyanates (D). Suitable hydrophilicizing agents (E) include at least one NCO-reactive group having a hydrogen that is active in accordance with the Zerewitinoff test and at least one hydrophilic or potentially hydrophilic group. Suitable NCO reactive groups, in particular include hydroxyl groups and primary and secondary amino groups. Hydrophilic groups include, inter alia, again hydroxyl groups, which are present in the hydrophilicizing agent or may come about as a result of groups present in the hydrophilicizing agent. Examples of preferred hydrophilic groups are the sulfo acid group and the phosphonic acid group. These are comparatively strongly dissociated relative to the carboxyl group and are, therefore, regarded as hydrophilic. They can be converted by neutralization into the ionic hydrophilic sulfonate and phosphonate groups, respectively, thereby raising the pH of the dispersion into the neutral or basic range, which is generally advisable. The carboxyl group is an example of a potentially hydrophilic group, since it dissociates but weakly and is, therefore, hardly hydrophilic, but is converted by neutralization almost entirely into the strongly dissociated, ionic hydrophilic carboxylate group. Another example of a potentially hydrophilic group is the tertiary amino group, which is converted by reaction (or neutralization) with an acid into the ionic hydrophilic, quaternary ammonium group. The hydrophilicizing agent (E) must, of course, only be employed in an amount such that sufficient isocyanate groups for the cross-linking reaction with the film-forming resin are retained.

A detailed description of the hydrophilicizing agents is presented in EP 0 537 578. Examples of suitable hydrophilicizing agents (E) include hydroxycarboxylic, hydroxysulfonic, hydroxyphosphonic, aminocarboxylic and aminosulfonic acids and tertiary aminoalkanols. Specific examples include glycolic acid, betaaminopropionic acid, hydroxyethanesulfonic acid, hydroxyethanephosphonic acid and N,N-dimethylaminoethanol. A particularly suitable hydrophilicizing agent (E) is dimethylolpropionic acid (DMPA), each of whose hydroxyl groups reacts with one isocyanate group and which is, therefore, able to link two molecules of polyisooyanate with an increase in the molecular weight and, if appropriate, in the NCO functionality as well. Probably as a result of steric hindrance, the carboxyl group is virtually inert with respect to the isocyanate groups under the reaction conditions.

Instead of reacting a hydrophobic polyisocyanate (C) to form a hydrophilically modified polyisocyanate (D) and mixing the latter with further hydrophobic polyisocyanate (C) for conjoint blocking, the mixture of the polyisocyanates (A) and (B) can also be produced by only partially hydrophilicizing an amount of hydrophobic polyisocyanate (C) corresponding to this mixture by reacting it with an amount of hydrophilicizing agent (E) which is such that the proportions of resultant, hydrophilically modified polyisocyanate (D) and of remaining hydrophobic polyisocyanate (C) correspond to the desired ratio of blocked hydrophilically modified polyisocyanate (A) to blocked hydrophobic polyisocyanate (B) for the finished dispersion, by converting any potentially hydrophilic groups by neutralization into ionic hydrophilic groups and by blocking the unreacted isocyanate groups of the hydrophilicizing mixture.

The Blocking of the Hydrorhilically Modified Polyisocyanate (A) and of the Hydrophobic Polyisocyanate (B)

The isocyanate groups of the hydrophilically modified polyisocyanate (D) and of the hydrophobic polyisocyanate (C) are blocked in conventional manner, in each case individually or, preferably, together, by reaction with appropriate blocking agents (F). Blocking is described, for example, in Progress in Organic Coatings 3 (1975), pages 73–99 and in Progress in Organic Coatings 9 (1981), pages 3–28. Use is made of the known blocking agents (F), which at from 20–120° C. enter with isocyanate groups into an addition reaction which is reversible at higher temperatures, so that the isocyanate groups that are then freed again are able to react with reactive groups of a film-forming resin. Examples of appropriate blocking agents (F) include secondary and tertiary alcohols, phenols, C-H-acidic compounds such as malonic acid derivatives, lactams, e.g., $\epsilon$-caprolactam and oximes. Preferred blocking agents include oximes such as formaldoxime, acetaldoxime, cyclohexanone oxime, acetophenone oxime, benzophenone oxime and, in particular, methyl ethyl ketoxime. Other blocking agents which can be used are 3,5-dimethylpyrazole and 1,2,4-triazole.

The Neutralizing Agent (H)

If a potentially hydrophilic group, for example a carboxyl group or a tertiary amino group, is introduced into the polyisocyanate by the hydrophilicizing agent (E), it can be converted by the neutralizing agent (H) into an ionic hydrophilic group. The neutralizing agent is a base if the potentially hydrophilic group is an acidic group, for example the carboxyl group, and is an acid in the case of basic potentially hydrophilic groups, for example a tertiary amino group. The bases can be inorganic bases such as ammonia or hydrazine, or organic bases. Preference is given to ammonia and to primary, secondary or tertiary amines, such as ethylamine, n-propylamine, dimethylamine, di-n-butylamine, cyclohexylamine, benzylamine, morpholine, piperidine and triethanolamine. Particular preference, because of their inert behavior relative to the blocked NCO functions, is given to tertiary amines such as N,N-dimethylethanolamine, N,N-diethylaminoethanol, triethylamine, tri-n-propylamine and tri-n-butylamine. Suitable acids preferably include carboxylic acids such as formic acid, acetic acid and benzoic acid.

The Auxiliary Solvent (G)

Preferred auxiliary solvents (G) include low-boiling inert solvents, which do not exhibit a miscibility gap with water, at least over wide ranges. These solvents have a boiling point at atmospheric pressure of <100° C. and can, therefore, be removed easily, if desired, by distillation down to a residual content of <2% by weight and, in particular, of <0.5% by weight, based on the finished dispersion, and reused. Examples of suitable such solvents include acetone, methyl ethyl ketone and tetrahydrofuran. Also suitable in principle are higher-boiling solvents such as n-butylglycol, di-n-butylglycol and N-methylpyrrolidone, which remain in the water-thinnable dispersion. However, they are less preferred because a particular advantage of the invention is that it is possible to prepare aqueous dispersions which are high in solids and stable even without environmentally polluting organic solvents.

The Preparation Process

Hydrophobic polyisocyanate (C) is first of all reacted with the hydrophilicizing agent (E), alone or in the presence of a catalyst. The hydrophobic polyisocyanate (C) is judiciously employed as a solution in an auxiliary solvent (G) with a solids content of from about 40–80% by weight. Suitable catalysts include organic tin salts such as dibutyltin diacetate or dibutyltin dilaurate. The reaction is started, for example, at room temperature and then the temperature is raised to up to 120° C. in order to complete the reaction. Such relatively high temperatures may in particular be necessary when blocking is conducted without solvent. When an auxiliary solvent (G) of appropriate boiling point is used as well, the reaction mixture can be heated at reflux for a time. It is preferable to operate at a temperature from 40–100° C. At these temperatures, the potentially hydrophilic groups of the hydrophilicizing agent (E) are generally inert, or virtually inert, with respect to the isocyanate group.

The hydrophilicizing agent is advantageously employed in an amount such that on average there is not more than one NCO-reactive function in the hydrophilicizing agent, intended for linking, per polyisocyanate molecule. In the case of dimethylolpropionic acid, therefore, not more than 1 mol of the acid is employed for 2 mol of polyisocyanate. It is advantageous to use about 1 equivalent of the NCO-reactive function that is intended for linking per mole of polyisocyanate. In each case, a mixture is formed that has statistical distribution of the hydrophilicizing groups. This mixture is regarded as a hydrophilically modified polyisocyanate (D) in the context of the invention, even if it does not include hydrophilically modified components.

To block the isocyanate functions it is also possible to treat a mixture of the resultant, hydrophilically modified polyisocyanate (D) and hydrophobic polyisocyanate (C), the latter being in turn, if desired, in the form of a from 40–80 percent strength by weight solution in an auxiliary solvent (G), with the blocking agent (F) in the stated proportion. As mentioned, the mixture to be blocked can also be produced by reacting hydrophobic polyisocyanate (C) with a corresponding excess of hydrophilicizing agent (E) and, if desired, with neutralizing agent (H). Alternatively, but less practically, the hydrophilically modified polyisocyanate (D) and the hydrophobic polyisocyanate (C) can each be blocked separately and the blocked products mixed. To make the mixing procedures easier it is possible in any case to add a quantity (or possibly a further quantity) of auxiliary solvent (G). Blocking takes place, depending on the blocking agent, at room temperature or judiciously at an elevated temperature of from 40–100° C. The blocking reaction leads to a temperature-dependent equilibrium. By means of guideline experiments it is possible without difficulty to determine the optimum temperature for a given polyisocyanate mixture (C) and (D) and a given blocking agent (F). The amount of blocking agent (F) depends on the number of isocyanate functions to be blocked. It is judicious to employ stoichiometric amounts, or a slight deficit, of blocking agent (F) in order to ensure complete reaction of the blocking agent, so that neither the product nor the auxiliary solvent (G) to be recycled is contaminated with blocking agent (F).

In principle it is also possible first of all to subject hydrophobic polyisocyanate (C) to partial blocking and then to react the remaining isocyanate groups with the hydrophilicizing agent (E), to convert any potentially hydrophilic groups into ionic hydrophilic groups, by neutralization, and to mix the resulting, blocked, hydrophilically modified polyisocyanate (A) with blocked, hydrophobic polyisocyanate (B). However, this is not advantageous, since the hydrophilicization reaction requires uneconomically long times because of the relatively low concentration of isocyanate groups.

If the hydrophilicizing agent (E) has initially introduced only potentially hydrophilic groups, the solution of the blocked polyisocyanates (A) and (B), as it is or following the addition of further auxiliary solvent (G), is neutralized in order to convert the potentially hydrophilic groups into ionic hydrophilic groups. As mentioned, it is generally advisable to neutralize more strongly acidic and, therefore, hydrophilic groups as well. In both cases, the neutralizing agent (H) is employed in stoichiometric amounts or else in deficient or excess amounts. In general, from 50–130 mol% of the amount required for complete neutralization is employed. By way of the amount of neutralizing agent it is possible to influence the viscosity of the dispersion. The greater the deficit, the less viscous the dispersion. On the other hand, the ionic hydrophilic groups formed as a result of neutralization promote the dispersion of the blocked polyisocyanates, so that not less than 50 mol% of neutralizing agent should be used. The optimum amount also depends on the proportion of blocked hydrophilically modified polyisocyanate (A) to blocked hydrophobic polyisocyanate (B) and for a particular dispersion can be determined by experiments without difficulty.

To prepare aqueous dispersions containing auxiliary solvent, water, which preferably has been deionized, is added to the neutralized solution, gradually or all at once. Alternatively, the neutralized solution is introduced, again gradually or all at once, into preferably deionized water. In both cases provision is made for intensive mixing, with or without the action of shear forces, thereby promoting the development of fine, stable dispersions. Intensive mixing is brought about, for example, with a propeller stirrer or with a dissolver. It is also possible to combine the operations of neutralization and dispersion, for example by adding the neutralizing agent (H) and the water simultaneously to the solution of the blocked polyisocyanates (A) and (B), it being possible for all or some of the neutralizing agent (H) to be dissolved in the water. The amount of water is preferably such that a dispersion with a solids content of from 35–80% by weight and a continuous phase containing aqueous auxiliary solvent is formed. It depends on the nature and the amount of the auxiliary solvent (G) and on the nature, proportion and degree of hydrophilicization of the polyisocyanates (A) and (B) and can be determined without difficulty by experiments. The amount of the auxiliary solvent in the dispersion is generally less than 25% by weight.

The auxiliary solvent-containing dispersions prepared in this way have the advantage over the conventional, water-free systems of a lower solvent content. In comparison with systems containing aqueous auxiliary solvent and external emulsifiers or protective colloids, they are advantageous because the ultimate coated film is markedly more resistant to moisture and the effects of weathering. In relation to systems containing aqueous auxiliary solvent and extensively or completely hydrophilicized polyisocyanates, the present dispersions have the same advantage; moreover, they are considerably less viscous, which facilitates their processing.

The dispersions virtually free from auxiliary solvent and having a solids content of from 35–60% by weight, advantageously from 40–50% by weight, that are prepared in the above-mentioned preferred embodiment of the process of the invention are particularly desirable. To obtain them, the overall amount of water is divided into two portions. First of all, a first portion is added to the neutralized solution of the blocked polyisocyanates (A) and (B). This first portion is such that when the auxiliary solvent (G) is removed there is no phase inversion, i.e. the water remains in dispersion or in solution in the continuous polyisocyanate phase. A sharp drop in viscosity is characteristic of the phase inversion. The maximum first portion of water which still does not lead to phase inversion depends essentially on-the desired solids content of the dispersion and on the nature of the polyisocyanates, their proportion and their degree of hydrophilicization, and can be determined without difficulty by experiments. In general it is not more than 75% of the overall amount of water. The optimum first portion of water is in general from 30–60% of the overall amount. The first portion of water can, like the solution of the polyisocyanates (A) and (B), be at room temperature at moderately elevated temperature such as 30–40° C., or else at a high temperature.

Following the addition of the first portion of water the temperature is raised, rapidly or gradually, to from 50–110° C. under atmospheric or reduced pressure, so that auxiliary solvent (G) is removed by distillation. During this procedure intensive mixing is again provided, as described above. This promotes the formation of a fine, stable dispersion and also brings about rapid and substantial removal of the auxiliary solvent (G). "Substantial removal" means that the content of auxiliary solvent (G) in the finished dispersion after adding the second portion of water is not more than 5% by weight. Then, under reduced pressure, it is possible to remove further auxiliary solvent (G) so that its content in the ready-to-use dispersion is <2% by weight, advantageously <0.5% by weight. However, it is more practical to remove the auxiliary solvent (G) even before adding the second portion of water, to such a substantial extent that its content in the finished dispersion, i.e, simply after the addition of the second portion of water, is <2% by weight, advantageously <0.5% by weight.

When the auxiliary solvent has been substantially removed, the second portion of water is added, gradually, at intervals or continuously. In this case intensive mixing as described above is provided, at least to the point of phase inversion, so that the resulting dispersion is sufficiently fine and stable. The temperature of the remaining water is advantageously in the range in which the temperature of the dispersion lies, while the auxiliary solvent (G) is removed, preferably at from 60–100° C. If superatmospheric pressure is used when adding the second portion of water, the temperature of the water may exceed 100° C. This makes the operation of dispersion easier, especially in the case of systems of relatively high viscosity. However, it is necessary in doing this to take note of the deblocking temperatures. Following the addition of the second portion of water, the dispersion is allowed to cool with stirring.

Stable and high-solids, aqueous dispersions are obtained that are virtually free from auxiliary solvent and which on storage at room temperature for 6 months or at 60° C. for from 4–8 weeks generally deposit less than 1% by mass of the solids they contain. This amount of solids, and any greater amounts of solids which may occasionally be deposited under suboptimal conditions, can be redispersed rapidly and durably by the action of appropriately high shear forces. Compared with aqueous dispersions that are virtually free from auxiliary solvent and have been prepared using emulsifiers or protective colloids, the present dispersions have the advantage that the ultimate coated films are more resistant to moisture and the effects of weathering. The same applies in comparison to corresponding dispersions in which there are relatively highly, or completely, hydrophilicized polyisocyanates; the latter, moreover, have a considerably higher viscosity, hindering their processing.

Using the Dispersions

The stable and high-solids aqueous dispersions of the invention, containing auxiliary solvent or virtually free from auxiliary solvent, are suitable as cross-linking agents for heat-cross-linking, storage-stable one-component coating systems, preferably for producing environmentally compatible, water-thinnable polyurethane coating systems by combination with aqueous film-forming resins, i.e. aqueous solutions, dispersions or emulsions and/or other water-thinnable systems comprising polymeric resins, having on average more than 1.5 NCO-reactive groups such as hydroxyl or amino groups, in each molecule. For this purpose the dispersions of the invention are combined with aqueous film-forming resins, preferably in amounts such that there is one NCO-reactive group of the film-forming resin per NCO group of the polyisocyanate. If desired, further cross-linkers known to those of skill in the art such as melamine resins, and/or known auxiliaries, for example, additives to enhance the leveling, the gloss and/or the adhesion of the coating, are mixed in, and the finished coating material is applied as it is or following dilution with water to adjust the viscosity, to the substrate in a usual manner. The coating is preferably first of all dried and then stoved at from 100–250° C. with elimination of the blocking agent, thereby cross-linking the film-forming resin.

Having generally described this invention, a further understanding can be obtained by reference to certain specific examples which are provided herein for purposes of illustration only and are not intended to be limiting unless otherwise specified.

EXAMPLE I 1.1 Preparing Hydrophilic Polyisocyanate

A 741 g amount of IPDI isocyanurate (VESTANAT®T 1890 from Huels AG) and 222 g of IPDI (VESTANAT®IPDI from Huels AG) are dissolved with stirring in 500 g of acetone. A 22.0 g amount of a 10% strength solution of dibutyltin dilaurate in acetone, as catalyst, and 134 g of pulverized dimethylolpropionic acid are added with stirring and the mixture is heated to about 60° C. so that it boils at reflux. It is stirred until all the dimethylolpropionic acid has dissolved and the NCO content of the solution (determined in accordance with DIN 53185) has fallen to 7.8–8.0%, which takes from 6–8 hours.

(1.2) Adding the Hydrophobic Polyisocyanate (C) and Blocking

A 1,482 g amount of IPDI isocyanurate (see section 1.1) and 3,000 g of acetone (for dilution) are added with stirring to the solution of section 1.1, which is just no longer boiling. The mixture is stirred at from 50–60° C. until a homogeneous solution is formed, this solution is cooled to from 40–55° C., and 783.0 g of methyl ethyl ketoxime are added with cooling at a rate such that the temperature remains in the range from 40–50° C. The batch is stirred at this temperature for a further 30 minutes and then cooled with stirring to 30° C.

(1.3) Dispersing the Blocked Polyisocyanate (A) and (B)

To the solution prepared as in section 1.2, 117 g of N,N-diethylaminoethanol and then, gradually and with stirring, 1,700 g of deionized water are added. The mixture is heated at from 80–95° C. in an open vessel. When almost all of the acetone has evaporated, another 2,700 g of deionized water which has been heated to from 70–85° C. is added with intensive mixing, by means of a propeller stirrer, almost continuously over the course of from 5–10 minutes. The resulting dispersion is then left to cool with stirring to 30° C.

A white dispersion is obtained having a solids content of 45% by weight (in accordance with DIN 53216 at 105° C.), an acetone content of 0.3% by weight (by headspace GC), a pH of 8.9 (in accordance with DIN 53785) and a viscosity at room temperature of 60 mPa·s (in accordance with DIN 53019 with D=200 s$^{-1}$). On storage for 6 months at room temperature or for 4 weeks at 50° C., there is no coagulation or sedimentation. The dispersion can be used without restrictions within this period.

EXAMPLE 2

(2.1) Preparing Hydrophilic Polyisocyanate (A), Adding the Hydrophobic Isocyanate (C) and Blocking The hydrophilic polyisocyanate is prepared as described in section 1.1, and 741 g of IPDI isocyanurate and 222 g of IPDI (as in Example 1) and, for dilution, 1,368 g of acetone are added with stirring to the solution which is just no longer boiling. Stirring is continued at from 50–60° C. until a homogeneous solution is formed, which is cooled to from 40–55° C., and 696 g of methyl ethyl ketoxime are added at a rate such that the temperature remains in the range from 40–50° C. The mixture is stirred at this temperature for a further 30 minutes and then allowed to cool with stirring to 30° C.

(2.2) Dispersing the Blocked Polyisocyanates (A) and (B)

A 80 g amount of N,N-dimethylaminoethanol and then 1,484 g of deionized water are added to the solution prepared in accordance with section 2.1. The mixture is heated with intensive mixing to from 75–85° C. and is substantially freed from acetone by reducing the pressure to from 800–900 mbar. Then four times 470 g of water preheated to from 70–80° C. are added slowly at short intervals, with further intensive mixing, and the resulting dispersion is left to cool with stirring to 30° C.

A white dispersion is obtained having a solids content of 44% by weight (in accordance with DIN 53216 at 105° C.), an acetone content of 0.3% by weight (by headspace GC), a pH of 8.8 (in accordance with DIN 53785) and a viscosity of 50 mPa·s (in accordance with DIN 53019 with D=200 s). On storage for 6 months at room temperature or for 4 weeks at 50° C., there is no coagulation or sedimentation. The dispersion can be used without restrictions within these periods.

EXAMPLE 3

(3.1) Preparing Hydrophilic Polyisocyanate (D)

A 1,482 g amount of IPDI isocyanurate (VESTANAT®T 1890 from Huls AG) is dissolved with stirring in 1000 g of acetone. 3.2 g of dibutyltin dilaurate as catalyst and 134 g of pulverized dimethylolpropionic acid are added with stirring and the mixture is heated to about 60° C. so that it boils at reflux. It is stirred until all the dimethylolpropionic acid has dissolved and the NCO content of the solution (in accordance with DIN 53185) has fallen to 6.1–6.3%, which takes from 6–8 hours.

(3.2) Adding the Hydrophobic Polvisocyanate (C) and Blocking

A 1,734g amount of HDI isocyanurate (DESMODUR® N 3300 from Bayer AG) and 2,500 g of acetone (for dilution) are added with stirring to the solution of section 3.1, which is just no longer boiling. The mixture is stirred at from 50–60° C. until a homogeneous solution is formed, this solution is cooled to from 40–55° C., and 1,131 g of methyl ethyl ketoxime are added with cooling at a rate such that the temperature remains in the range from 40 . 50° C. The batch is stirred at this temperature for a further 30 minutes and then the solution of the blocked polyisocyanates is cooled to 30° C.

(3.3) Dispersing the Blocked Polvisocyanates (A) and (B)

To the solution prepared as in section 3.2, 89 g of N,N-dimethylaminoethanol and then, gradually and with vigorous stirring, 2,000 g of deionized water are added. The mixture is heated to from 75–90° C. with intensive mixing and is substantially freed from acetone by reducing the pressure to from 800–900 mbar. Then, almost continuously, a further 4,200 g of deonized water that has been heated to from 80–90° C. are added with further intensive mixing over the course of from 10–20 minutes.

A white dispersion is obtained having a solids content of 42% by weight (in accordance with DIN 53216 at 105° C.), an acetone content of 0.4% by weight (by headspace GC), a pH of 8.9 (in accordance with DIN 53785) and a viscosity of 250 mPa·s (in accordance with DIN 53019 with D=200 s$^{-1}$). On storing the dispersion over a period of 6 months at room temperature or of 4 weeks at 50° C., there is no coagulation or sedimentation. The dispersion can be used without restrictions during these periods.

(3.4) Example 4 (non-inventive comparison example)

The initial procedure is as described under sections 1.1 and 1.2, and 89 g of N,N-dimethylaminoethanol and then 4,112 g of deionized water that has been heated to from 30–40° C. are added all at once to the solution of the blocked polyisocyanates (A) and (B). The mixture is substantially freed from acetone with intensive mixing at from 50–60° C. under reduced pressure. Even during this procedure, there soon occur inhomogenities and precipitation of solids. Ultimately, complete phase separation occurs. The white, paste-like mass that has deposited cannot be redispersed.

Obviously numerous modifications and variations of the present invention are possible in light of the above teachings. It is, therefore, to be understood that within the scope of the appended claims, the invention may be practiced otherwise than as specifically described herein.

What is claimed as new and is desired to be secured by Letters Patent of the United States is:

1. A process for preparing stable and high-solids aqueous dispersions of blocked isocyanates, containing auxiliary solvent, which comprises:

(1) preparing a solution of a polyisocyanate mixture of from 20–70% by weight of a blocked, hydrophilically modified polyisocyanate (A), wherein, in the preparation of blocked, hydrophilically modified polyisocyanate (A), a polyisocyanate starting material is not first subjected to partial blocking and then reacted with hydrophilicizing agent and wherein the blocked, hydrophilically modified polyisocyanate (A) is a blocked, ionic hydrophilically modified polyisocyanate which forms as a result of complete or partial neutralization of a polyisocyanate having a carboxyl group which is neutralized by ammonia or an amine, and from 30–80% by weight of a blocked, hydrophobic polyisocyanate (B) in an auxiliary solvent (G); and (2) adding to this solution, with intensive mixing, an amount of water which is such as to give a two-phase system comprising a disperse polyisocyanate phase and a continuous, aqueous phase containing auxiliary solvent.

2. A process for preparing stable and high-solids aqueous dispersions of blocked isocyanates, containing auxiliary solvent, which comprises:

(1) preparing a solution of a polyisocyanate mixture of from 20–70% by weight of a blocked, hydrophilically modified polyisocyanate (A), wherein, in the preparation of blocked, hydrophilically modified polyisocyanate (A), a polyisocyanate starting material is not first subjected to partial blocking and then reacted with hydrophilicizing agent, and from 30–80% by weight of a blocked, hydrophobic polyisocyanate (B) in an auxiliary solvent (G), wherein the mixture of the polyisocyanates (A) and (B) is produced by only partially hydrophilicizing an amount of hydrophobic polyisocyanate (C) corresponding to this mixture by reacting it with an amount of hydrophilicizing agent (E) which is such that the proportions of resultant, hydrophilically modified polyisocyanate (D) and of remaining hydrophobic polyisocyanate (C) correspond to the desired ratio of blocked hydrophilically modified polyisocyanate (A) to blocked hydrophobic polyisocyanate (B) for the finished dispersion, by converting any potentially hydrophilic groups by neutralization into ionic hydrophilic groups and by blocking the unreacted isocyanate groups of the hydrophilicizing mixture; and (2) adding to this solution, with intensive mixing, an amount of water which is such as to give a two-phase system comprising a disperse polyisocyanate phase and a continuous, aqueous phase containing auxiliary solvent.

3. A process for preparing stable and high-solids aqueous dispersions of blocked isocyanates, containing auxiliary solvent, which comprises:

(1) preparing a solution of a polyisocyanate mixture of from 20–70% by weight of a blocked, hydrophilically modified polyisocyanate (A), wherein, in the preparation of blocked, hydrophilically modified polyisocyanate (A), a polyisocyanate starting material is not first subjected to partial blocking and then is reacted with a hydrophilicizing agent which is a hydroxycarboxylic, hydroxysulfonic, hydroxyphosphonic, aminocarboxylic or aminosulfonic acid or a tertiary aminoalkanol, and from 30–80% by weight of a blocked, hydrophobic polyisocyanate (B) in an auxiliary solvent (G) of acetone, methyl ethyl ketone, tetrahydrofuran, n-butylglycol, di-n-butylglycol or N-methylpyrrolidone, and wherein the polyisocyanate parent of each of polyisocyanates (A) and (B) is a diisocyanate selected from the group consisting of 1,6-diisocyanatohexane (HDI), bis(4-isocyanatocyclohexyl)methane (HMDI), 1,5-diisocyanato-2-methylpentane (MPDI), 1,6-diisocyanato-2,4,4-trimethylhexane and/or 1,6-diisocyanato-2,2,4-trimethylhexane (TMDI), 3-isocyanatomethyl-3,5,5-trimethylcyclohexyl isocyanate (IPDI), uretdione thereof, polyisocyanates having more than two isocyanate groups per molecule prepared by allophanatization, trimerization, biuretization or urethanization of the diisocyanates with polyhydric alcohols, with polyfunctional polyamines, the triisocyanurates prepared by trimerizing the diisocyanates, or aromatic polyisocyanates; and (2) adding to this solution, with intensive mixing, an amount of water which is such as to give a two-phase system comprising a disperse polyisocyanate phase and a continuous, aqueous phase containing auxiliary solvent.

* * * * *